United States Patent
Eronen et al.

(10) Patent No.: US 10,278,666 B2
(45) Date of Patent: May 7, 2019

(54) SYSTEMS AND METHODS OF AUTOMATED DOSE CONTROL IN X-RAY IMAGING

(71) Applicant: PaloDEx Group Oy, Tuusula (FI)

(72) Inventors: Esa Eronen, Karina (FI); Markus Rintamäki, Tuusula (FI); Martti Kalke, Tuusula (FI)

(73) Assignee: PaloDEx Group Oy, Tuusula (FI)

( * ) Notice: Subject to any disclaimer, the term of this patent is extended or adjusted under 35 U.S.C. 154(b) by 749 days.

(21) Appl. No.: 14/304,378

(22) Filed: Jun. 13, 2014

(65) Prior Publication Data

US 2015/0359501 A1 Dec. 17, 2015

(51) Int. Cl.
*A61B 6/00* (2006.01)
*A61B 6/03* (2006.01)
(Continued)

(52) U.S. Cl.
CPC .............. *A61B 6/542* (2013.01); *A61B 6/032* (2013.01); *A61B 6/14* (2013.01); *A61B 6/4085* (2013.01); *A61B 6/466* (2013.01); *A61B 6/488* (2013.01); *A61B 6/5211* (2013.01); *A61B 6/5258* (2013.01); *A61B 6/08* (2013.01);
(Continued)

(58) Field of Classification Search
CPC ..... A61B 6/5205; A61B 6/5258; A61B 6/542; A61B 6/032; A61B 6/08; A61B 6/14; A61B 6/4085; A61B 6/4441; A61B 6/463; A61B 6/465; A61B 6/466; A61B 6/467; A61B 6/469; A61B 6/488; A61B 6/5211; A61B 6/544
See application file for complete search history.

(56) References Cited

U.S. PATENT DOCUMENTS 5,680,430 A 10/1997 Khutoryansky et al.
5,867,555 A 2/1999 Popescu et al.
(Continued)

FOREIGN PATENT DOCUMENTS

CN 102451014 A 5/2012
EP 1172069 A1 1/2002
(Continued)

OTHER PUBLICATIONS

International Search Report and Written Opinion in corresponding International Application No. PCT/IB2015/001261 dated Oct. 27, 2015.
(Continued)

*Primary Examiner* — Chih-Cheng Kao
(74) *Attorney, Agent, or Firm* — Andrus Intellectual Property Law, LLP

(57) ABSTRACT

X-ray imaging systems and methods for exposure control in three-dimensional X-ray imaging include acquiring at least one image with an X-ray emitter and an X-ray receiver. At least one physical characteristic of the object to be imaged is determined from the at least one image. At least one exposure parameter value based is determined based upon the at least one physical characteristic of the object to be imaged. The X-ray emitter and X-ray receiver acquire a plurality of projection images about the object to be imaged using at least one exposure parameter value. A three-dimensional X-ray image is reconstructed from the plurality of projection images.

19 Claims, 12 Drawing Sheets

(51) Int. Cl.
*A61B 6/14* (2006.01)
*A61B 6/08* (2006.01)

(52) U.S. Cl.
CPC ............ *A61B 6/4441* (2013.01); *A61B 6/463* (2013.01); *A61B 6/465* (2013.01); *A61B 6/467* (2013.01); *A61B 6/469* (2013.01); *A61B 6/544* (2013.01)

(56) References Cited

U.S. PATENT DOCUMENTS

| | | | |
|---|---|---|---|
| 6,023,495 A * | 2/2000 | Adler | ............... A61B 6/032 378/4 |
| 7,042,977 B2 | 5/2006 | Dafni | |
| 7,558,364 B2 | 7/2009 | Lin | |
| 7,756,243 B2 | 7/2010 | Gohno | |
| 8,270,760 B2 | 9/2012 | Miao et al. | |
| 2004/0062341 A1 | 4/2004 | Popescu et al. | |
| 2005/0249329 A1 * | 11/2005 | Kazama | ............... A61B 6/032 378/16 |
| 2006/0018435 A1 | 1/2006 | Toth et al. | |
| 2007/0053477 A1 | 3/2007 | Ning | |
| 2007/0076842 A1 * | 4/2007 | Tkaczyk | ............... A61B 6/032 378/5 |
| 2007/0110210 A1 * | 5/2007 | Nishide | ............... A61B 6/032 378/4 |
| 2007/0258559 A1 | 11/2007 | Hur | |
| 2007/0286332 A1 | 12/2007 | Gohno et al. | |
| 2009/0122952 A1 | 5/2009 | Nishide et al. | |
| 2009/0168950 A1 * | 7/2009 | Jianying | ............... A61B 6/032 378/8 |
| 2012/0224665 A1 | 9/2012 | Chandrashekarappa et al. | |
| 2013/0101079 A1 | 4/2013 | Hough et al. | |
| 2015/0190102 A1 * | 7/2015 | Bruno | ............... A61B 6/14 378/39 |

FOREIGN PATENT DOCUMENTS

| | | |
|---|---|---|
| EP | 2394579 A1 | 12/2011 |
| JP | 2008012229 A | 1/2008 |
| WO | 2009156943 A1 | 12/2009 |
| WO | 2011137374 A1 | 11/2011 |
| WO | 2013049818 A1 | 4/2013 |
| WO | 2013103790 A1 | 7/2013 |

OTHER PUBLICATIONS

Pauwels, et al. "Future prospects for dental cone beam CT imaging." Imaging in Medicine from Academic OneFile, Oct. 2012, website visited Sep. 8, 2015, http://go.galegroup.com/ps/i.do?id=GALE%7CA308984657&v=2.1&u=navyship&it=r&p=GPS&sw=w&asid=c3e2346a63342b36bff99c2d22323a68.

International Preliminary Report on Patentability for PCT/IB2015/001261, dated Dec. 22, 2016.

* cited by examiner

SYSTEMS AND METHODS OF AUTOMATED DOSE CONTROL IN X-RAY IMAGING

FIELD

The present disclosure relates to X-ray imaging systems and methods.

BACKGROUND

PCT Patent Application Publication No. WO2009156943 discloses an imaging generation device with optimized dose control that includes a noise determination unit for determining a distribution of noise in a projection domain of a region of interest and a dose control unit for determining a dose profile for a radiation source of the imaging generation device based on a determined distribution of noise by using a noise propagation algorithm.

U.S. patent application Ser. No. 13/409,912 discloses a method to reduce radiation dose delivered by an imaging system. In the method, a virtual mask representation is selected based on a shape of an organ to be masked. The virtual mask representation is displayed on a scout image. A radiation dose to be delivered is manipulated so as to modify the virtual mask representation to obtain an optimum attenuation profile.

PCT Application Publication No. WO2013049818 discloses a method of consistent and verifiable optimization of computed tomography (CT) radiation dose. Mathematical models allow for estimation of patient size, image, size-specific radiation dose, and image quality targets based on digital image data and radiologist preferences. An automated system processes the image and dose data according to the mathematical models and stores and displays the information, enabling verification and ongoing monitoring of consistent dose optimization. An optimization model calculates specific scanner settings needed to attain target image quality at the minimum radiation dose possible.

U.S. Pat. No. 7,082,183 discloses computed tomography dose indexing phantom selection for dose reporting. A control mechanism in communication with an X-ray source and detector assembly includes logic that is adapted to execute at least one scout scan of the object to produce a first scout scan image. An elliptical patient model is generated based on the first scout scan image. The elliptical patient model is matched to a phantom diameter approximation. A dose report is generated based on the phantom diameter approximation. The dose report is displayed.

SUMMARY

The present disclosure results from the present inventors' research and development of improved X-ray imaging systems and methods. The inventors have realized that prior art X-ray systems and methods, including the systems and methods described herein above, often are not user friendly and can be inefficient and ineffective. The inventors have recognized that it is desirable to provide improved X-ray systems and methods that automatedly determine imaging exposure parameters. In an embodiment, an operator may input a designated quality and exposure parameters are determined therefrom. In additional embodiments, the X-ray system and methods determine physical characteristics of the object and field of view to be imaged and exposure parameter are determined therefrom. The inventors have also recognized that it is desirable to provide improved X-ray systems and methods that limit excessive radiation to a patient being imaged. The inventors have realized that X-ray system operators may image patients at exposure parameters that produce X-ray images of a higher quality (e.g. less noise), resulting in greater exposure, than is necessary for intended purposes of the images. This can result in wasting time and applying excessive radiation to the patient.

The present disclosure provides X-ray systems and methods that overcome disadvantages in the prior art.

An exemplary embodiment of a method of exposure control in three-dimensional X-ray imaging includes acquiring at least one scout image with an X-ray emitter and an X-ray receiver. A computer processor determines at least one physical characteristic of the object to be imaged from the at least one scout image. The computer processor determines at least one exposure parameter value based upon the determined at least one physical characteristic of the object to be imaged. The X-ray emitter and X-ray receiver acquire a plurality of projection images about the object to be imaged using the at least one imaging parameter value. The computer processor reconstructs a three-dimensional X-ray image from the plurality of projection images.

In an additional exemplary embodiment of a method of exposure control in three-dimensional X-ray imaging includes acquiring at least one scout image with an X-ray emitter and an X-ray receiver. The X-ray emitter operates at an initial imaging parameter value. A computer processor determines at least one physical characteristic of the object to be imaged from the at least one scout image. A user input of image quality is received. The computer processor determines a new imaging parameter value based upon the determined at least one physical characteristic of the object to be imaged and the user input of image quality. The X-ray emitter and X-ray receiver acquire a plurality of projection images about the object to be imaged using the X-ray emitter operating at the new imaging parameter value. The computer processor reconstructs a three-dimensional X-ray image from the captured plurality of projection images.

An exemplary embodiment of an X-ray imaging system includes an X-ray emitter configured to produce X-rays relative to an imaging parameter value and direct the X-rays towards an object to be imaged. An X-ray receiver is configured to receive X-rays from the X-ray emitter. The X-ray emitter and X-ray receiver are configured to acquire at least one scout image of the object to be imaged. An input device is configured to receive a user input of image quality. A computer processor is communicatively connected to the X-ray emitter, X-ray receiver, and the input device. The computer processor is configured to determine a physical characteristic of the object to be imaged from the at least one scout image. The computer processor is configured to determine a new imaging parameter value from the physical characteristic and the user input of image quality. The X-ray emitter and X-ray receiver are configured to acquire a plurality of projection images about the object to be imaged using the new imaging parameter value. The computer processor is configured to reconstruct a three-dimensional X-ray image from the captured plurality of projection images.

DETAILED DESCRIPTION OF THE DRAWINGS

In the present description, certain terms have been used for brevity, clearness and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. No limitation in the appended claims is intended to invoke interpretation under 35 U.S.C. § 112(f) unless the terms "means for" or "step for" are explicitly recited in the respective limitation.

Embodiments of the systems and methods as disclosed herein operate to automatically calculate exposure parameter values for use in a 3D imaging procedure of a patient. As disclosed in more detail herein, embodiments can determine optimal exposure parameter values which may include, but are not limited to kilovolts (kV) and milliamps (mA) provided to the X-ray emitter. Embodiments may achieve this by determining physical characteristics of the patient, for example head size and/or density. Physical characteristics of size and/or density affect the total attenuation of X-rays by the object to be imaged. In still further embodiments, optimal noise filtering may also be automatedly determined. Some embodiments acquire scout images for patient positioning and field of view (FOV) identification purposes, and those scout images can also be used as inputs for automated determination of imaging parameter values. Thus, it may not be necessary to acquire additional scout images for the determination of the exposure parameters.

Figure 5A:
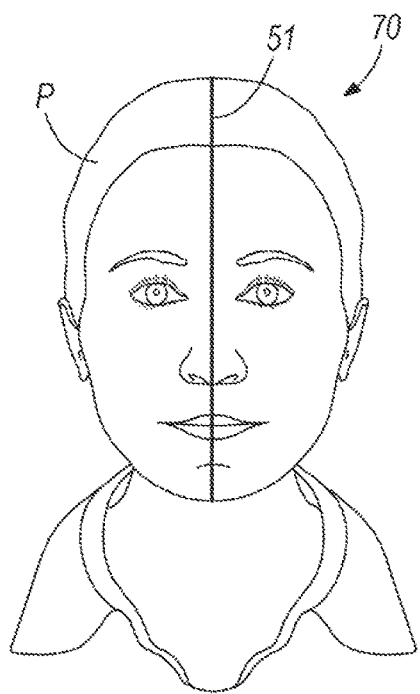
FIG. 5A is a view of midsagittal positioning lights.
Figure 5B:
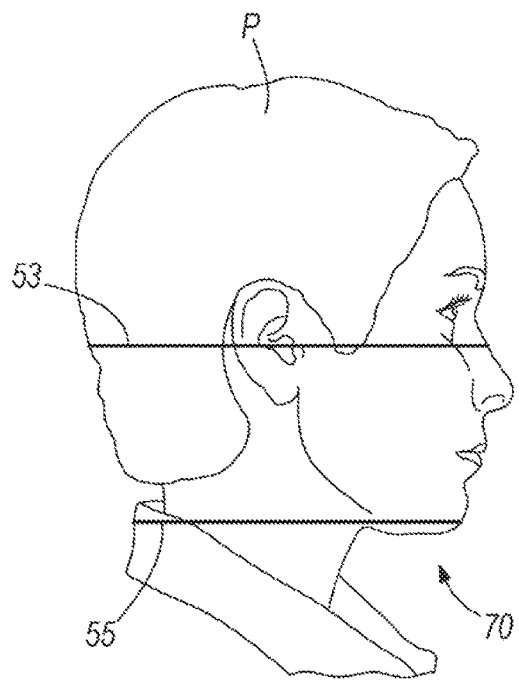
FIG. 5B is a view of horizontal positioning lights.

FIGS. 1A-1D depict an exemplary X-ray imaging apparatus 20 for acquiring X-ray images of an object, including for example a dental or medical patient P (see e.g., FIGS. 5A and 5B). In the particular example shown, the imaging apparatus 20 is configured for 3-D imaging of the dento-maxillofacial complex of the human skull; however other configurations of apparatuses for imaging of other portions of the object can instead be employed with the concepts of the present disclosure. The X-ray imaging apparatus 20 can optionally be configured to conduct different types of imaging procedures, for example panoramic imaging (for example standard, pediatric, ortho zone, wide arch, orthogonal, and/or the like), cephalometric imaging (for example cephalo pediatric lateral projection, cephalo lateral projection, cephalo postero-anterior, and/or the like). In a presently used exemplary embodiment, the X-ray imaging apparatus 20 is used for 3D imaging, exemplarily cone beam computed tomography (CBCT) 3D imaging. The Figures depict just one example of an X-ray imaging apparatus for use with the concepts in the present disclosure. Other examples of X-ray imaging apparatus can also be employed.

The exemplary imaging apparatus 20 has a housing 22 that is movably supported on a support column 24. The housing 22 can be moved up and down in the vertical direction V via a conventional guide motor (not shown) that is configured to move the housing 22 vertically up and down along a track 26 extending along support column 24. The housing 22 includes a generally vertically extending guide section 28 disposed on the support column 24 and a generally horizontally extending support section 30 extending generally horizontally from the guide section 28. The support section 30 supports a rotating section 32 (sometimes referred to as a "gantry"), which is rotatable in a horizontal plane H with respect to the stationary support section 30, as shown at arrow 34 in FIG. 1D. The support section 30 and/or rotating section 32 contain a conventional guide motor (not shown) configured to rotate the rotating section 32, as shown at arrow 34. In an alternate example, the apparatus can be mounted to a support structure including for example a wall instead of or in addition to being supported by a column.

An X-ray emitter housing 36 and an X-ray receiver housing 38 are opposed from each other and extend generally vertically from the rotating section 32. The emitter housing 36 contains an emitter generally located at 40 and supported in the emitter housing 36 and positioned to emit X-rays through the object being imaged (e.g. the patient P) to a receiver located at 42 and supported in the X-ray receiver housing 38. In general, the emitter comprises an X-ray with a cathode and an anode. A power source (not depicted) produces a voltage, exemplarily in kilovolts (kV) across the cathode and anode to accelerate electrons from the cathode to the anode (not depicted). A current exemplarily in milliamps (mA) between tha cathode and the anode generally determines the amount of electrons emitted from the cathode. The anode comprises a target, which may exemplarily be made of tungsten that is generally angled so that electrons from the cathode striking the target will produce X-rays generally in the direction out of the emitter towards the receiver.

A patient positioning housing 44 extends from the guide section 28 and includes a chin support 48 for positioning the head of the patient P between the opposed emitter 40 and receiver 42. A head support 46 extends from the support section 30 through the rotating section 32. The chin support 48 and head support 46 are optional and other means for positioning the patient can be employed. A patient positioning panel 68 is located on the patient positioning housing 44 and receives user inputs for adjusting the position of various components of the imaging apparatus 20, as will be discussed further herein below.

A control panel 50 is attached to the housing 22 and is configured to receive user inputs for controlling the imaging apparatus 20 and to provide a display of functionalities of the imaging apparatus 20, as will be described further herein below. Optionally, the control panel 50 can be supported by an arm 49 that pivots about the imaging apparatus 20 for positioning in the positions shown in FIGS. 1A and 1B-D, respectively.

Figure 1A:
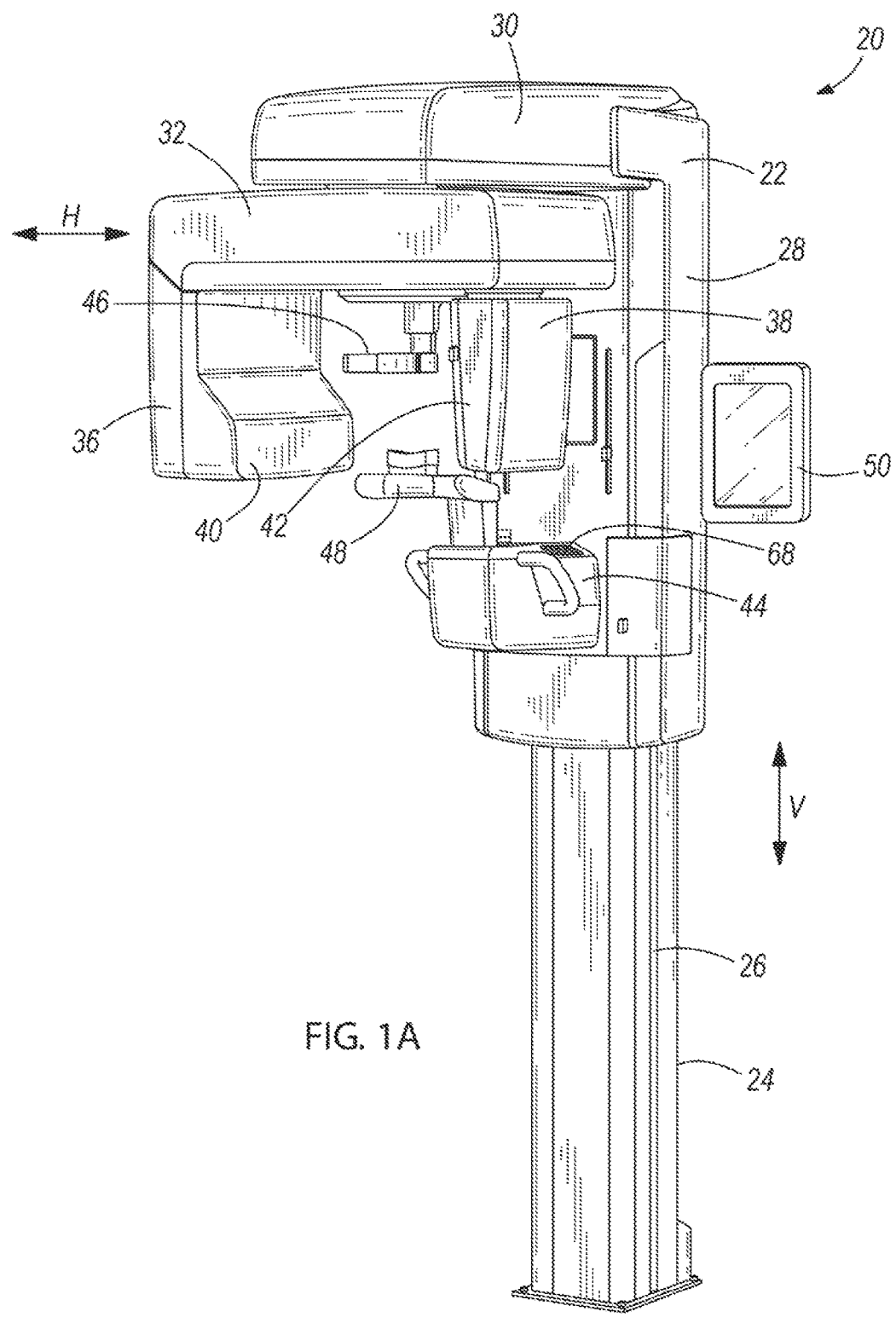
FIG. 1A is a perspective view of an exemplary X-ray imaging apparatus.
Figure 1B:
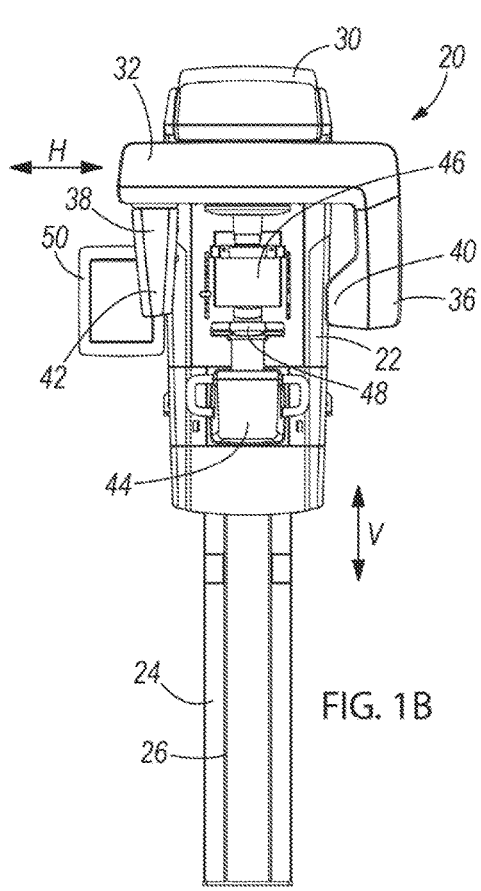
FIG. 1B is a front elevation view of the exemplary X-ray imaging apparatus.
Figure 1C:
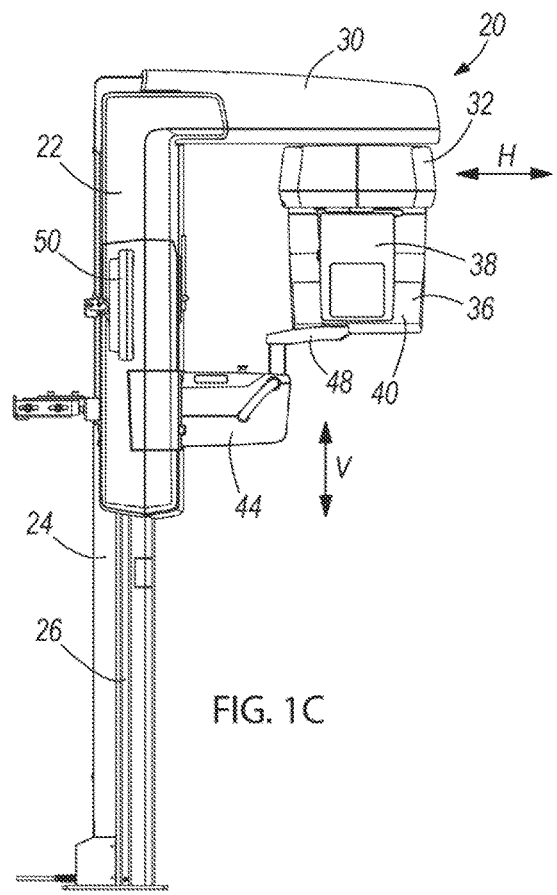
FIG. 1C is a side elevation view of the exemplary X-ray imaging apparatus.
Figure 1D:
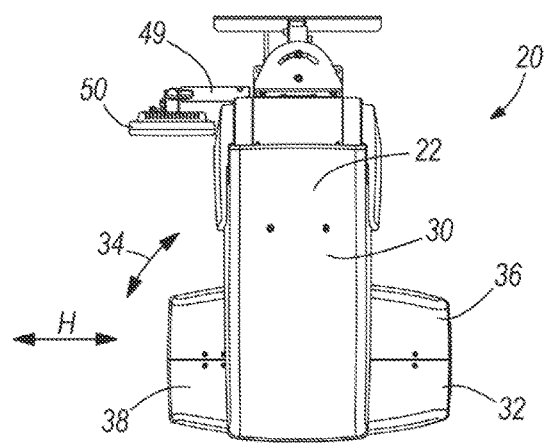
FIG. 1D is a top view of the exemplary X-ray imaging apparatus.
Figure 2:
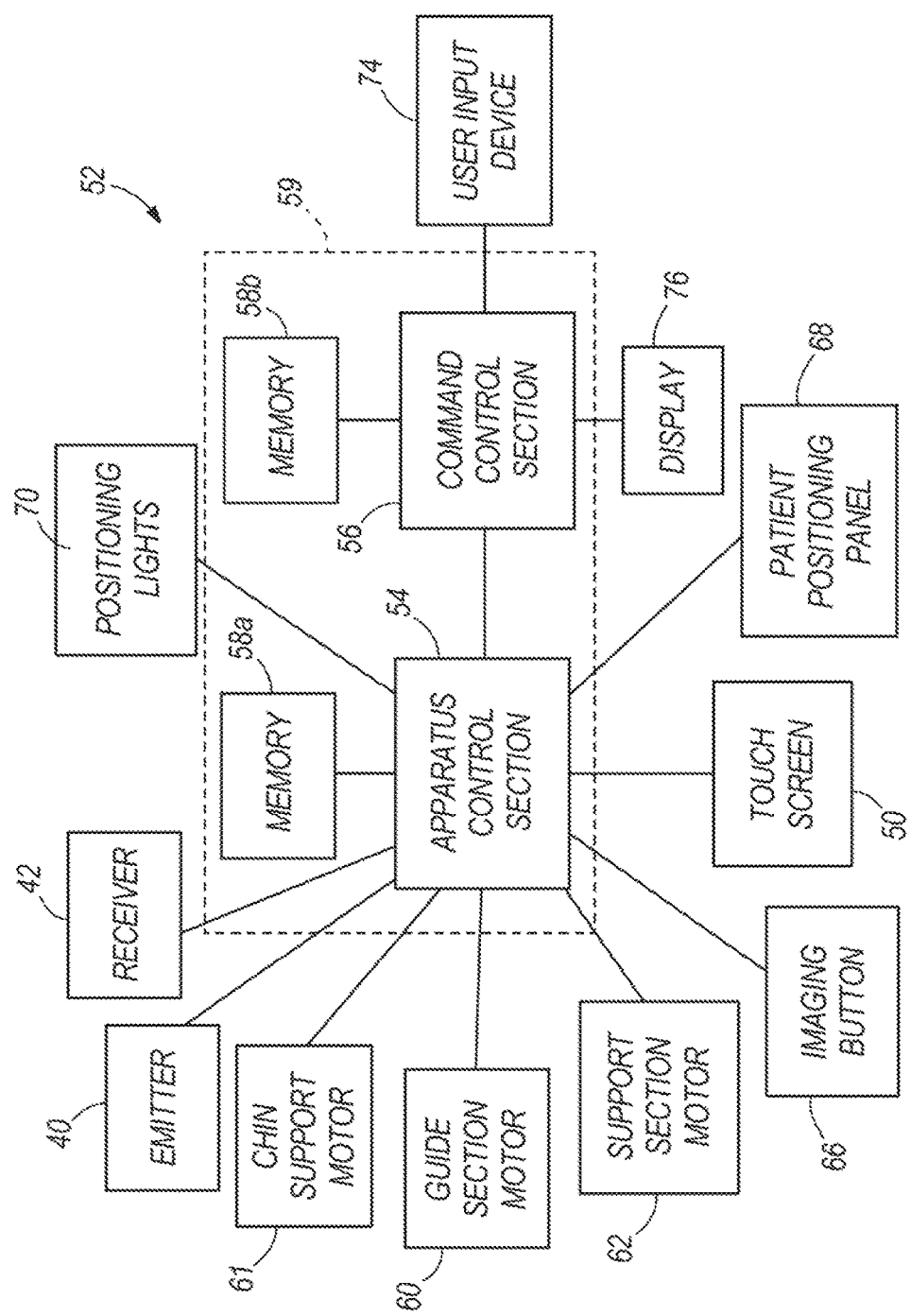
FIG. 2 is a schematic representation of portions of an exemplary X-ray imaging system.

FIG. 2 schematically depicts portions of an exemplary embodiment of an X-ray imaging system 52 that incorporates the X-ray imaging apparatus 20. The system 52 includes, among other things, a control circuit 59 that includes an apparatus control section 54 and a command control section 56. In embodiments, the control circuit 59 is one or more computer processors. The one or more computer processors may include integrated memory or be communicatively connected to memory upon which computer readable code is stored, the execution of the code by the one or more computer processors cause the computer processors to carry out the functions as disclosed herein. The apparatus control section 54 and command control section 56 each include a memory 58a, 58b, respectively. In addition, both the apparatus control section 54 and command control section 56 are programmable and can send and receive computer commands via wired or wireless links, including for example the links shown in solid-line format in FIG. 2. The command control section 56 can send electronic signals/commands to the apparatus control section 54 and can receive electronic signals/commands from the apparatus control section 54. Similarly, the apparatus control section 54 can send computer electronic signals/commands to the command control section 56 and can receive electronic signals/commands from the command control section 56. Although the example shown in FIG. 2 depicts two control sections 54, 56 that function together, alternative arrangements could include only one control section or more than two control sections that function together by sending and/or receiving commands to and from each other, respectively. Control sections 54, 56 may be software modules operating on a single computer processor, or may be separate computer processors respectively executing command and/or apparatus control computer readable code. The examples described in the present disclosure are not limited to the specific system 52 arrangements and configurations depicted in FIG. 2.

Figure 4:
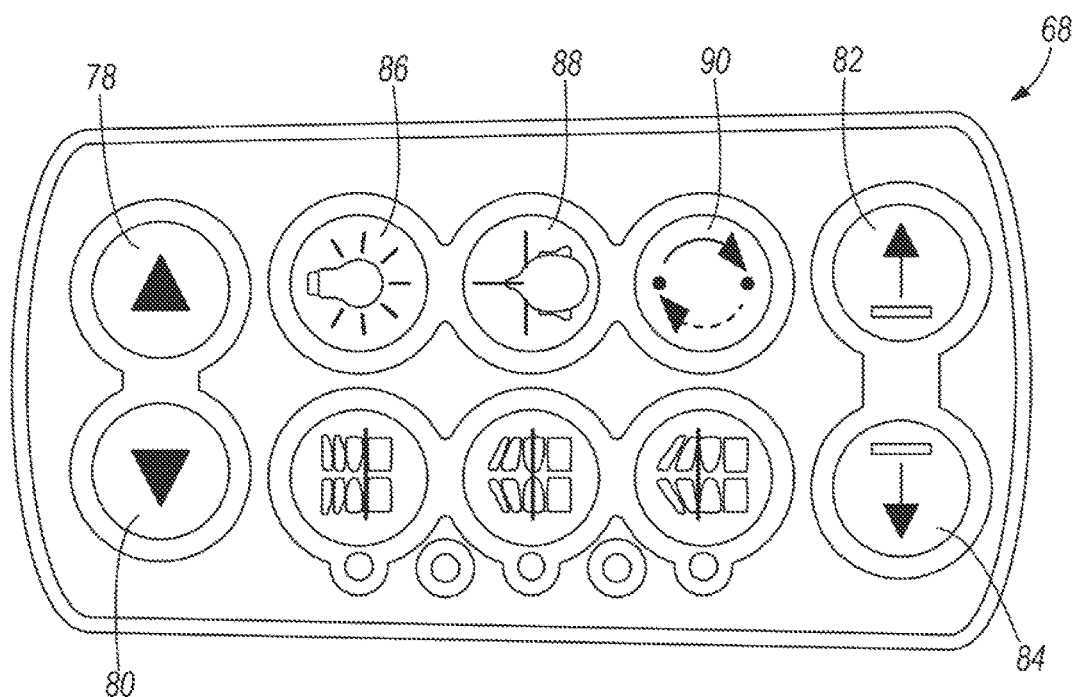
FIG. 4 is a view of a patient positioning panel.

In the exemplary embodiment in FIG. 2, the apparatus control section 54 is collocated with the X-ray imaging apparatus 20 and controls various functionalities of the X-ray imaging apparatus 20. For example, the apparatus control section 54 communicates via electronic signals/commands with the memory 58a; with a guide section motor 60 for causing movement of the guide section 28 along the support column 24; with a support section motor 62 for causing rotational movement of the rotating section 32; with a chin support motor 61 for causing movement of the chin support 48; and with the touch screen display 50 for displaying apparatus characteristics and functionalities and for receiving user inputs, as will be discussed further herein below. Optionally a head support motor (not shown) can also be included for causing movement of the head support 46. In addition, the apparatus control section 54 can receive commands from a user input device 74, including for example the imaging button 66 shown in FIGS. 2 and 7 and from the patient positioning panel 68 shown in FIG. 4. Operation of the user input device 74 and the patient positioning panel 68 will be described further herein below.

The apparatus control section 54 also sends and receives electronic signals/commands with the emitter 40 and receiver 42 to control the emitter 40 and receiver 42 and obtain imaging data that can be converted into X-ray image(s) of the object being imaged (e.g., patient P). In use, the apparatus control section 54 receives patient positioning inputs from the patient positioning panel 68 and sends corresponding command signals to the guide section motor 60, support section motor 62, and chin support motor 61 to position the apparatus 20 with respect to the patient P. The system 20 can include more or fewer motors and movable sections than what is shown and described and in some examples can provide complete three-dimensional movement of the apparatus 20 with respect to the patient P. In another example, the apparatus control section 54 can receive patient positioning inputs from the patient positioning panel 68 and send corresponding command signals to move the patient P with respect to the apparatus 20, via for example a chair that is movable by a conventional chair guide motor (not shown). In a further example, the apparatus control section 54 can control the relative positioning of both the apparatus 20 and a chair guide motor to achieve a user-desired position. To facilitate easier positioning of the apparatus 20 with respect to the object being imaged, the apparatus control section 54 can also be configured to control positioning lights 70 (see e.g. FIGS. 2, 5A and 5B) for identifying on the object being imaged a field of view that is desired for imaging, as will be described further herein below. In additional embodiments, the patient and/or apparatus 20 may be positioned manually relative to one another.

Figure 3:
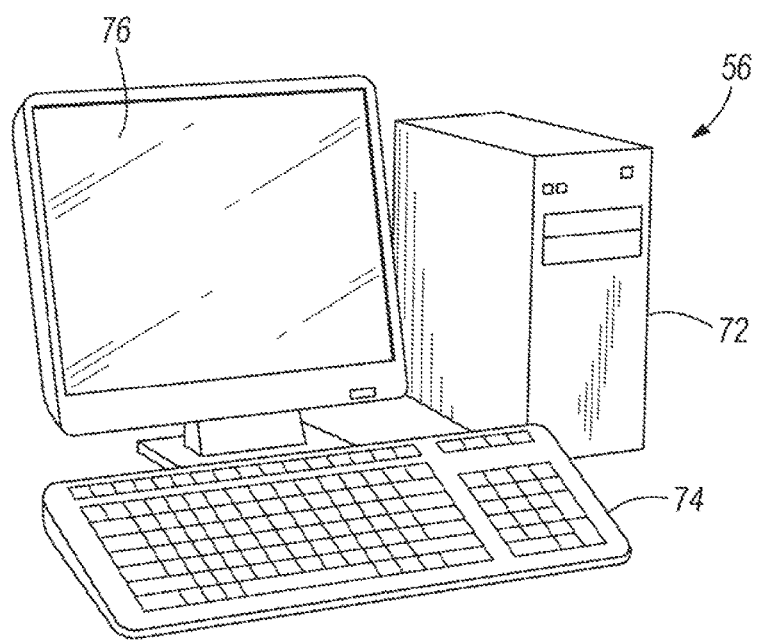
FIG. 3 is a perspective view of an exemplary command control section and display.

The apparatus control section 54 is also configured to communicate with the command control section 56, to receive electronic signals/commands from the command control section 56, and to provide image data received from the receiver 42 to the command control section 56. Referring to FIG. 3, an exemplary command control section 56 can be a personal computer 72 having a user input device 74, which in the example shown is a keyboard, and having a display 76, which in the example shown is a computer monitor. Other types of command control sections, user input devices and displays are contemplated and are within the scope of the present disclosure. For example, the display 76 and input device 74 can instead or also comprise a touch screen device, a mouse, a handheld computer device and/or the like.

Referring to FIGS. 1A-D, 4, 5A, and 5B, a patient P is initially positioned in the apparatus 20 between the emitter 40 and receiver 42. In the example shown, the patient P is positioned with the chin on the chin support 48 and with the head on the head support 46. Next, the patient positioning panel 68 is manually operated to instruct the apparatus control section 54 to control the apparatus 20 and position the apparatus 20 into a position that is generally appropriate for X-ray imaging of the patient P. This can be done by for example the guide section motor 60, chin support motor 61, and/or support section motor 62, as described above. In the example shown in FIG. 4, pressing input key 86 turns on the positioning lights 70 as shown in FIGS. 5A and 5B, to assist in the aforementioned positioning of the patient P. FIGS. 5A and 5B depict exemplary positioning lights 70, including a midsagittal light 51 and horizontal top and bottom lights 53, 55, respectively, delineating a desired field of view for the X-ray process. Additional patient positioning lights 70 can be employed. Use of positioning lights 70 is optional and other configurations for positioning than that shown may be used. Pressing input key 88 on the patient positioning panel 68 signals the apparatus control section 54 that positioning instructions are going to be input by the user and causes the apparatus to rotate into a position for further patient positioning.

Pressing arrows 78, 80 on the patient positioning panel 68 instructs the apparatus control section 54 to move the apparatus 20 up and down, respectively. The user can thus watch the positioning lights 70 and use the arrows 78, 80 and 82, 84 to position the lights 70 (and thus the apparatus) into an appropriate position on the patient P. Pressing input keys 78, 80 instructs the apparatus control section 54 to control the respective support section motor 62 to move the apparatus 20. Pressing arrows 82, 84 instructs the apparatus control section 54 to control the chin support motor 61 to move the chin support 48 up and down, respectively. As mentioned above, it is also recognized that instead of moving the X-ray apparatus 20, it is possible to utilize different configurations wherein for example the patient P is moved with respect to the apparatus 20 instead of or in addition to the configuration described above wherein the apparatus 20 is moved with respect to the patient P. Pressing input key 90 after imaging causes the apparatus 20 to rotate into a position where the patient can easily get out of the apparatus 20.

Figure 6:
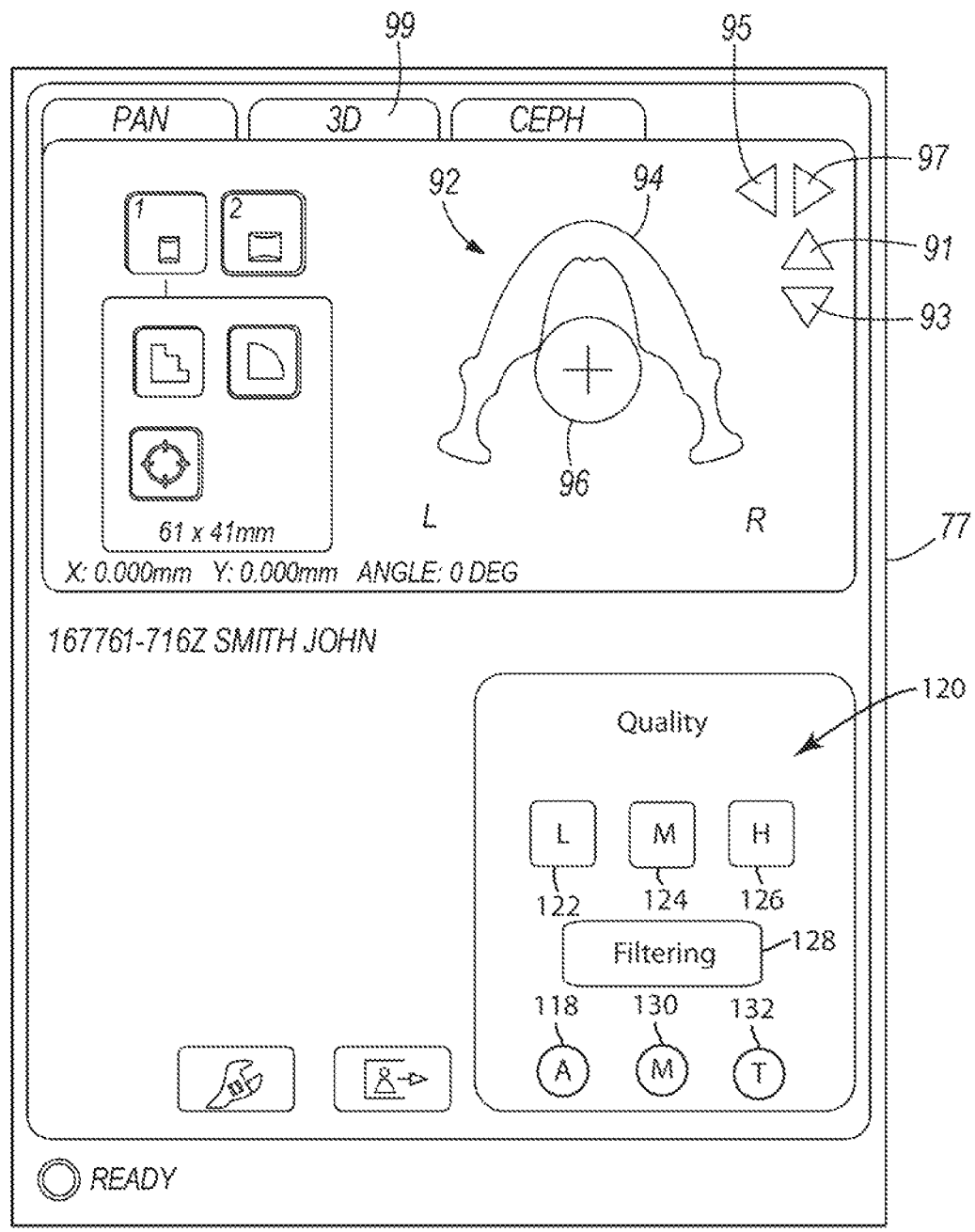
FIG. 6 is an exemplary embodiment of a graphical user interface (GUI) as may be used as an input device in connection with systems and methods.

Referring to FIG. 6, once the patient P is generally positioned with respect to the apparatus 20 so as to generally achieve a desired field of view for an imaging process, for example 3-D imaging, the command control section 56 controls the display 76 to visually present a graphical user interface (GUI) 77 that includes a presentation of an initial view 92 of the object, representing in this example the anatomy of the patient P to be imaged. The GUI 77 that includes the initial view 92 can also or instead be displayed on the touch screen display 50, as controlled by the apparatus control section 54, or on another graphical display device, for example a handheld device, television screen and/or the like. In the example shown in FIG. 6, the initial view 92 includes a generic model 94 of a patient's jaw. In an additional example, the initial view 92 can include a picture or an X-ray image of the object, for example a particular anatomy of the patient P. In a merely exemplary embodiment of this additional example, an initial X-ray can be taken with the X-ray imaging apparatus 20 to generate the initial view 92 for viewing by the user.

In the example shown in FIG. 6, a position marker 96 is shown in the GUI 77. The position marker 96 illustrated in FIG. 6 has a circular shape and crosshairs; however, other configurations of the position marker may be utilized. The position marker 96 indicates a particular 3-D volume that is desired for imaging. In an embodiment, the position marker 96 indicates a center of a volume to be imaged. The position marker 96 overlaps the initial view 92 and is movable in the GUI 77 with respect to the initial view 92. In an additional embodiment, the position marker 96 can also be resized to convey the volume of the region to be imaged. In an alternate example, the initial view 92 can be movable with respect to the position marker 96. In another example, both the initial view 92 and position marker 96 can be movable with respect to each other. Relative movement of the initial view 92 and position marker 96, as described above, can be requested via the input device 74 and/or via positioning keys on a touch screen configuration, for example touch screen display 50, including for example up and down arrows 91, 93 and left and right arrows 95, 97. Other configurations for modifying the presentation of the initial view 92 in the GUI 77 can be utilized, for example by voice commands, a mouse pad, drag-and-drop touch screen commands, and/or the like.

Input keys are also provided on the GUI 77 for selecting between panoramic, 3-D, and cephalometric imaging modalities. The present example relates to 3-D imaging, which can be selected at input key 99; however the principles disclosed herein could be applied in other imaging modalities, as described herein above.

Figure 7:
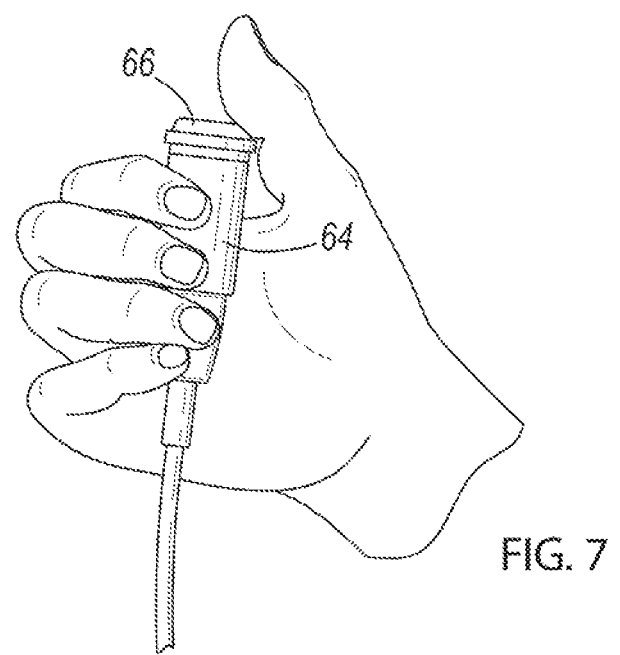
FIG. 7 is a perspective view of an input device.

Referring to FIGS. 6 and 7, the GUI 77, including the initial view 92, can thus be modified by the user to identify a specific area of interest on the initial view 92 of which the user desires a 3-D image. The user modifies the GUI 77 by moving the position marker 96 to the area of interest on the initial view 92 and in an additional embodiment, may adjust the size of the position marker 96 to encompass a desired volume to be imaged. The user may then operate the input device 64 by pressing imaging button 66, which instructs the apparatus control section 54 to control the imaging apparatus 20, including for example the guide section 28, support section 30 and rotating section 32 to move into a position with respect to the patient P that is commensurate with the position marker 96 on the initial view 92. The apparatus 20 is thus positioned wherein the emitter 40 and receiver 42 operate to obtain one or more scout images of the patient P that correspond to the relative positioning of the position marker 96 and initial view 92 on the GUI 77.

Figure 8:
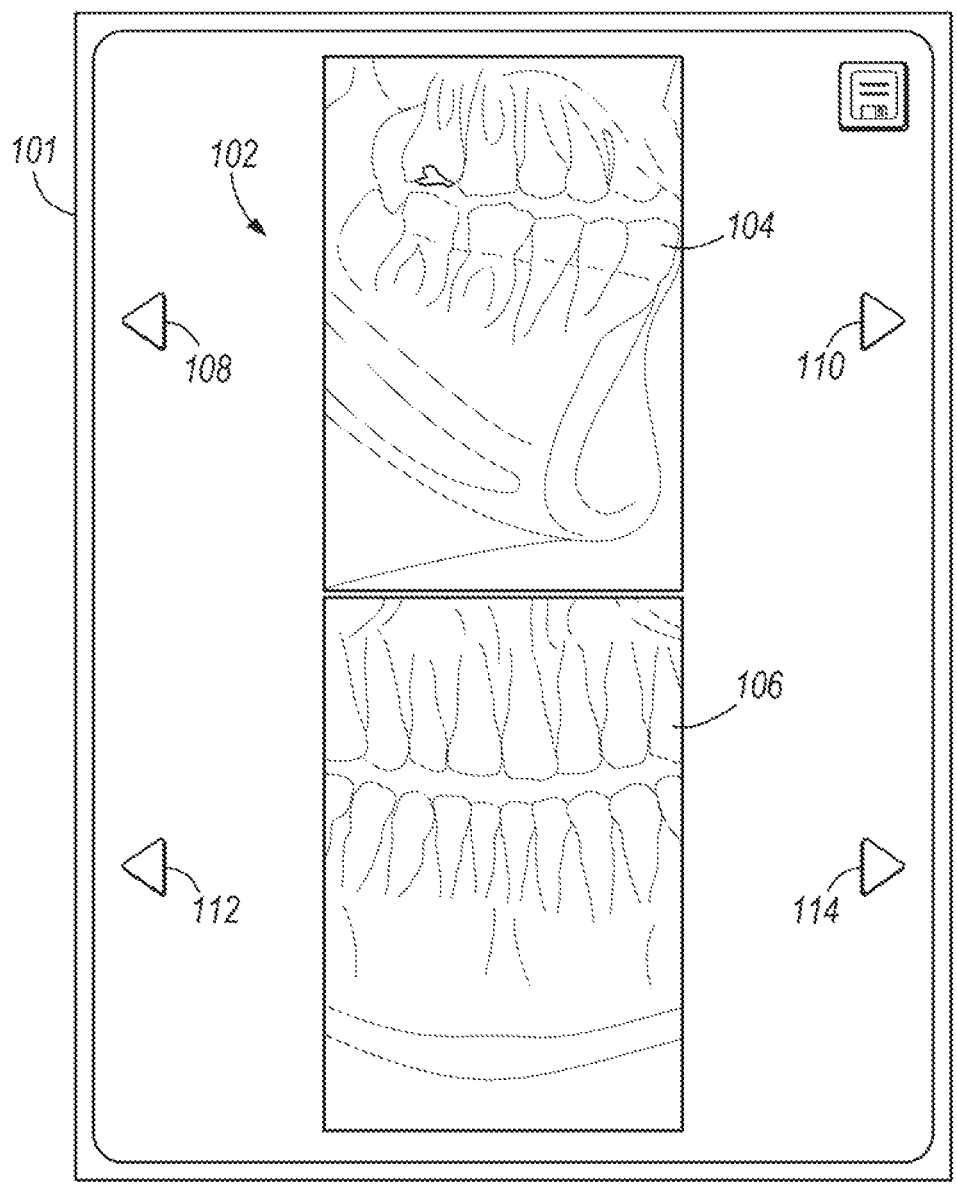
FIG. 8 is a display of positioning images of the object being imaged.

In an embodiment, the control circuit 59 is programmed to operate the emitter and receiver in accordance with the user modifications to the initial view at 92 in order to acquire at least one scout image of the patient, which is exemplarily depicted at FIG. 8. FIG. 8 depicts a graphical display 101 that presents scout images that may be taken in accordance with the user inputs described above. In embodiments one or more scout images may be acquired and used for patient positioning. The scout images 102 include a first scout image 104 and a second scout image 106, although a person of ordinary skill in the art will recognize that in alternative embodiments more or fewer scout images may be acquired. It is also recognized that while in some embodiments, scout images may be limited to a portion of the patient dentomaxillofacial area, in other embodiments a larger portion of the patient, including, but not limited to the entire head of a patient may be imaged in the scout images. The scout images 102 are exemplarily taken of the patient from different angles, which in the example shown are an orthogonal view 104 and a tangential view 106. Some exemplary embodiments as disclosed herein, use the at least one scout image, already acquired for patient positioning purposes as described herein, to further automatedly determine at least one exposure parameter value. In still other embodiments, the at least one scout image may be used only for processing purposes and not presented to the user.

Referring back to FIG. 6, in embodiment as described in further detail herein, the X-ray imaging system may be operated to provide automatic dose control (ADC). The systems and methods of ADC as described in further detail herein provide the functionality and benefit of automatedly determining at least one exposure parameter value for use in 3D X-ray imaging from the at least one scout image. In embodiments as disclosed herein, X-ray dose to the patient may be optimized while relying on less technical user input. In an embodiment, the user selects the automated dose control feature or mode of operation by selecting the "A" button 118 while the initial view is presented in the GUI 77. In embodiments, the imaging system may also operate in a manual mode (by selection of the "M" button 130) or in a test mode (by selection office "T" button 132). In an example of a manual mode, the exposure settings are manually selected. In an example of a test mode, a specific predetermined combination of exposure settings is selected. Upon initiation of the ADC mode the user is prompted to enter a desired image quality in the GUI 120. It is to be recognized that the GUI 120 may change to present an interface configured to receive inputs specifically directed to the selected mode of operation. In an exemplary embodiment, the user inputs a desired image quality by selecting a low button 122, a medium button 124, or a high button 126 in order to select between low, medium, and high quality images to be acquired.

Exemplarily, desired image quality as used herein is representative of the noise found in the acquired X-ray projection images or alternatively, a signal to noise ratio of the acquired X-ray projection images. In still further embodiments, the user inputs a desired quality/noise level for the resulting 3D image reconstruction. As described in further detail herein, the noise in the X-ray projection images is a function of the physical characteristics of the object/patient to be imaged (e.g. size, density, or attenuation) and the exposure parameters used to operate the X-ray imaging apparatus (e.g. mA, kV, exposure time, duty cycle, number of projection images, voxel size, and the reconstruction system and/or software). In some embodiments, a user may also be prompted to input whether image noise reduction software filtration is to be used in the 3D reconstruction process, exemplarily by selecting or not selecting a "filtering" button 128. In still further exemplary embodiments, a user may provide an input representative of an amount of filtering, exemplarily high, medium, or low filtering is to be used. In general, it will be recognized that image noise reduction software filtration results in images that have the same noise level or quality to those taken with greater X-ray exposure, but possibly at the cost of reduced resolution. Therefore, the addition of image noise reduction software filtration, or the use of higher filtration can result in achieving suitable image quality with reduced X-ray exposure to the patient. It will be recognized that depending upon the purpose of the imaging, the user may select an appropriate level of quality and/or resolution/filtering only as is needed to achieve the purpose of the images to be taken.

In an exemplary and non-limiting embodiment, automated dose control (ADC) can be carried out dependent upon image quality and be based upon "mA compensation." In such an embodiment, mA compensation may be where the system increases a strength of the projection image filtration when a user reduces emitter current (mA). Such an embodiment may find application with adult patients when an operator evaluates that less emitter current is enough for a particular task (e.g. willing to accept the resulting compromise with image quality). In such an embodiment, a filtration is automatically selected so that the image noise level keeps constant or is partially compensated with other emitter current values or reduces an increase in noise resulting from the lowered emitter current.

Figure 9:
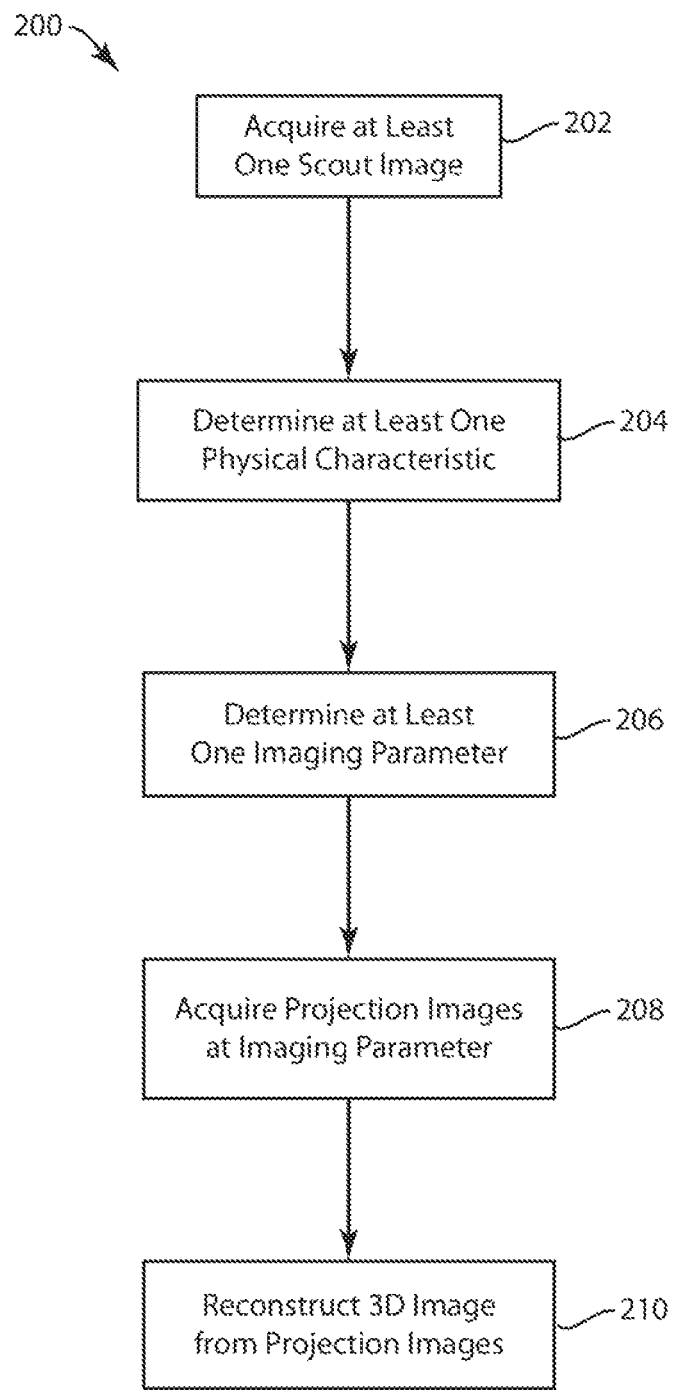
FIG. 9 is a flow chart depicting one example of a method of automatic dose control in an X-ray imaging apparatus.
Figure 10:
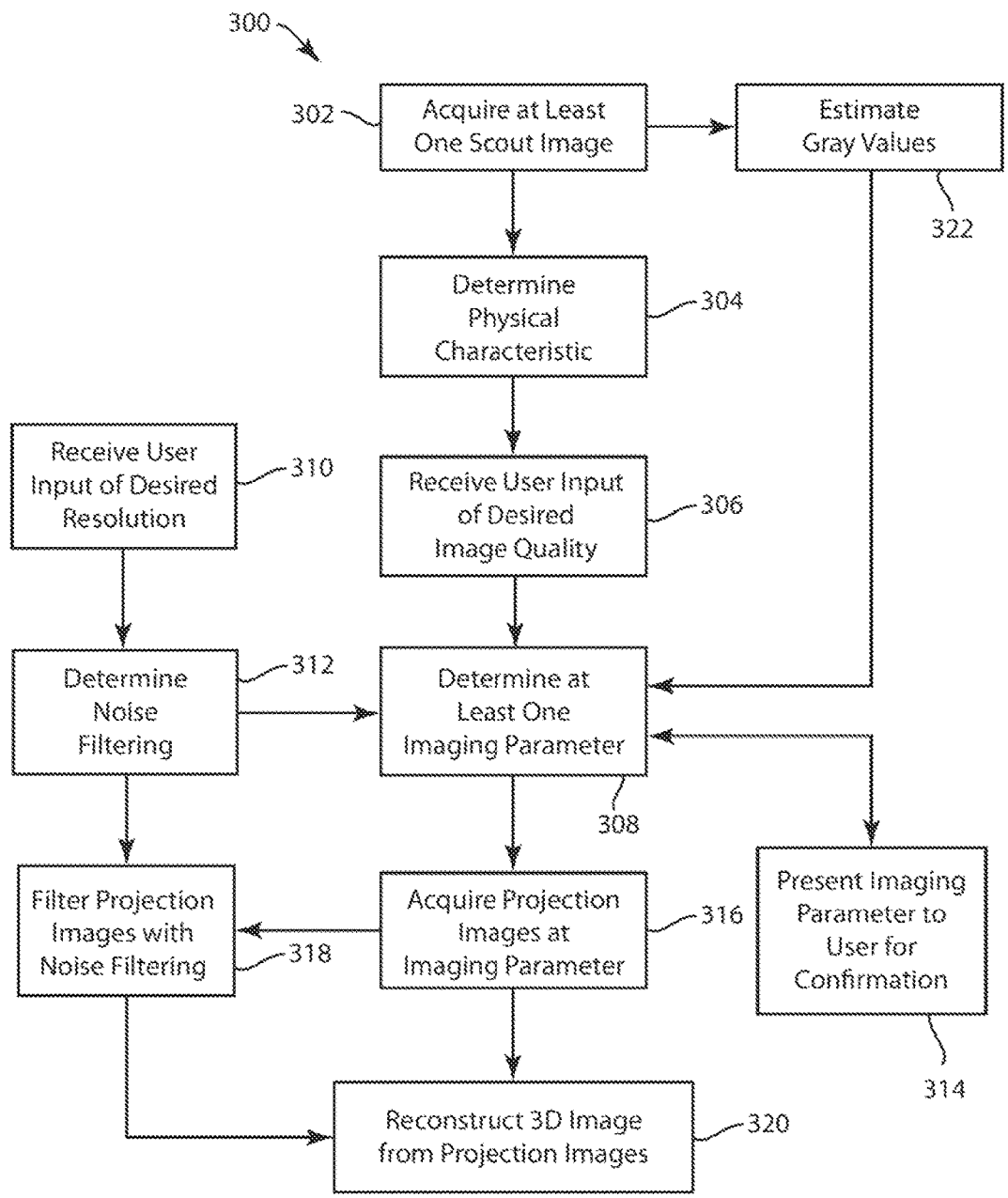
FIG. 10 is a flow chart depicting another example of a method of automatic dose control in an X-ray imaging apparatus.
Figure 11:
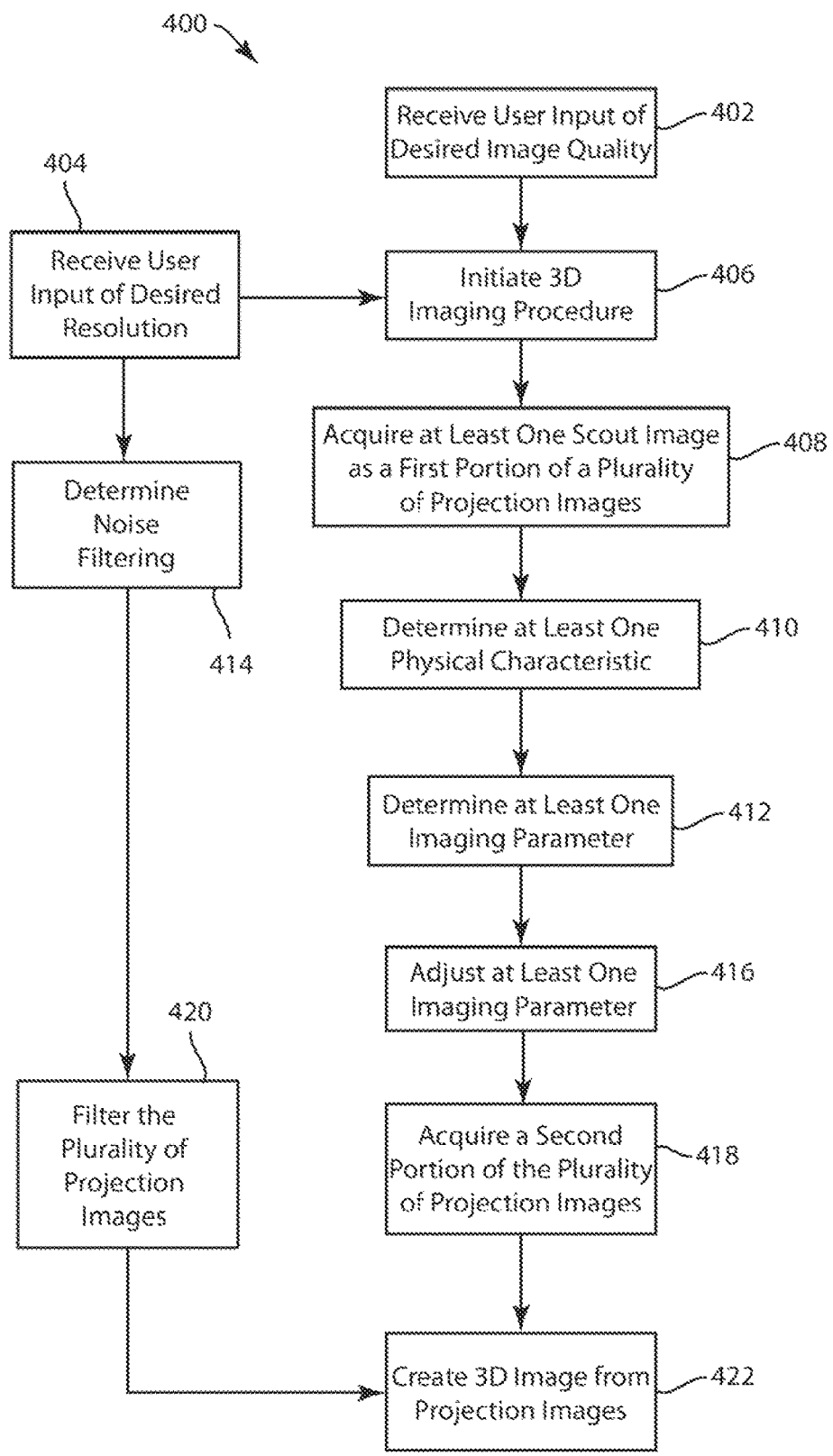
FIG. 11 is a flowchart depicting another example of a method of automatic dose control in an X-ray imaging apparatus.

FIGS. 9-11 are flow charts that depict exemplary embodiments of methods of automatic dose control in an X-ray imaging apparatus.

FIG. 9 depicts an exemplary embodiment of a method 200 of automatic exposure control in an X-ray imaging apparatus. The method 200 begins at 202 when at least one scout image is acquired. As described above, the acquisition of at least one scout image may occur after a generalized area for imaging or an initial view has been selected. In still further embodiments, the at least one scout image may be a previously acquired image, including, but not limited to, a CBCT image, panoramic, or cephalometric image of the patient. Alternatively, or in addition, scout images may be acquired after a patient has been properly positioned in the X-ray imaging apparatus as described above, and the user exemplarily selects 3D X-ray imaging and a field of view (FOV) size on the X-ray imaging apparatus. However, it will be recognized by a person of ordinary skill in the art that a variety of preparatory steps may be taken before at least one scout image is acquired at 202. In embodiments, the at least one scout image can be any image capable of being used as described herein, including, but not limited to at least one projection image acquired for the purpose of patient positioning, at least one image acquired for the specific purpose of automatic dose control, or at least one image acquired during the course of an imaging procedure. Therefore, the systems and methods as disclosed herein may use any of a variety of images as scout images independent of the purpose for which the image was initially obtained, provided that the image is suitable for automatic dose control purposes. In an embodiment, the at least one scout image(s) is acquired at default values for the exposure parameters identified above, so long as the values of the exposure of parameters used are known and can be used as disclosed in further detail herein. In embodiments, the acquired scout images may be used to position the patient and/or select a refined FOV for the 3D imaging.

Next, at 204, at least one physical characteristic of the object to be imaged, or a portion of the object to be imaged, is determined based on one or more characteristics of the at least one scout image (for example, without limitation, brightness, contrast, noise level, and/or visible anatomical features) and one or more of the exposure parameters used to take the scout image(s). A merely exemplary comparative example will be used herein to highlight distinctions and feature of the methods as described herein, comparatively between 3D imaging of the head of a child patient versus 3D imaging of the head of an adult patient. In an exemplary additional embodiment, the determination is of a level of noise in the image which may be caused by the at least one physical characteristic of the object. In an exemplary embodiment, the physical characteristic determined at 204 is at least one of a size, density, or attenuation of the object to be imaged. It will be recognized that a head of a child patient will usually be smaller, less dense, and exhibit less attenuation in the at least one scout image as compared to at least one scout image of the head of an adult patient, when the at least one scout images are acquired at the same exposure parameter values. As noted above, if the exposure parameter values used to obtain the at least one scout images are known, the size, density, or attenuation of the objected imaged in the scout images can be determined at 204.

Next, at least one exposure parameter value is determined at 206. As previously described above, the exposure parameters may include a variety of parameters, including, but not limited to emitter voltage, emitter current, a number of projection images, a voxel size, a reconstruction system or software, an exposure time, and/or a duty cycle. Values for one or more of these exposure parameters can be determined at least in part from the determined physical characteristic from 204. In an exemplary embodiment, the emitter voltage, number of projection images, and voxel size may be fixed or predefined with values for use in association with the ADC operation. With these exposure parameters predetermined, both patient dose and X-ray image quality (as defined by a noise level) are functions of the emitter current (mA) at 206. A value of emitter current may be therefore determined at least in part based on the physical characteristics determined at 204. A larger, denser object to be imaged will result in more attenuation which requires greater emitter current to achieve the purpose of the X-ray images. Therefore, increased size, density, or attenuation of the object to be imaged results in an increased value for the at least one exposure parameter.

At 208, the least one exposure parameter value determined at 206 is used to acquire a plurality of projection images. The plurality of projection images are exemplarily acquired at the exposure parameter value by rotating the X-ray emitter and receiver incrementally about the head of the patient while capturing a series of X-ray projection images at these rotated intervals while operating the emitter or other portions of the X-ray imaging system at the exposure parameter value.

Finally, at 210 a 3D image is reconstructed from the acquired plurality of projection images. The reconstruction of the 3D image may be achieved using a variety of reconstruction techniques. In an exemplary embodiment, an iterative reconstruction technique, for example algebraic reconstruction technique (ART) that beings with an initial reconstruction and iteratively refines the reconstruction based upon additional information from the projection images, may be used. In additional embodiments, a non-iterative reconstruction technique, for example, filtered back projection (FBP), may be used. It is to be recognized that embodiments of the method 200, as described above, as well as the exemplary embodiments of the methods 300 and 400 as described in further detail herein, may be carried out without each of the steps as disclosed herein, or may be carried out in conjunction with additional steps not depicted in the specific flowcharts of those Figures while remaining within the scope of the present disclosure. Still further embodiments may conduct operations and functions as disclosed herein in alternative orders while remaining within the scope of the present disclosure.

FIG. 10 is a flowchart of an additional exemplary embodiment of a method 300 of automatic dose control in an X-ray imaging apparatus. More specifically, the exemplary embodiment of the method 300 depicts one embodiment in which a user is prompted for or provides user inputs that are used to further refine the automatic dose control features.

Similar to that as described above with respect to the method 200, the method 300 begins with the acquisition of at least one scout image at 302. After the at least one scout image is acquired at 302, some optional embodiments may receive a selection of a field of view (FOV) as described above with respect to FIGS. 6 and 8. Continuing with the method 300, at 304, at least one physical characteristic value is determined by analyzing the at least one scout image, and in particular, the selected field of view in the at least one scout image. As noted above with respect to the method 200, the at least one physical characteristic can be determined from the scout images to include a value for an object size, density or attenuation and this determination of a physical characteristic value at 304 may be facilitated in embodiments wherein the at least one scout image is acquired at default or known exposure parameter values which can then be used to exemplarily determine an amount of attenuation experienced in the at least one scout image. In an additional embodiment, separate scout images are used for patient positioning and for ADC calculations. In a merely exemplary embodiment, additional scout images or scout images from one or more particular angles may be needed for the attenuation calculations as disclosed in further detail herein.

In embodiments of determining the physical characteristic at 304 the required number of scout images from the at least one scout image may depend upon the specific application of physical structure or structures being imaged. In an embodiment, a sufficient number of scout images are analyzed such that the scout images cover the full object to be imaged and a reliable estimate of the object attenuation can be made. In an exemplary embodiment, the determined physical characteristic may be an average noise level (e.g. pixel standard deviation value) or an average density (e.g. pixel mean value). In embodiments, the determination of physical characteristics at 304 is facilitated if at least one scout image is acquired at known or referenced exposure parameter values. In an exemplary embodiment, the at least one scout image is acquired at a reference emitter current that is selected to result in a known noise level in the reconstructed volume of a known reference object size. In comparison to this reference emitter current and resulting noise level, a determined lower emitter current as explained in further detail herein would result in a nosier reconstruction image and a higher emitter current would result in a reconstructed image with less noise. Similarly, the determination of exposure parameters as described in further detail herein in embodiments is dependent upon establishing connection between the reconstructed image quality (e.g. noise level) and the at least one physical characteristic determined at 304 from the scout image, which may include a noise level of the scout image. If the emitter current used to acquire the at least one scout image is constant across scout images between different patients, then the size, density, and attenuation of the object to be imaged is a considerable factor in a quality of later acquired projection images and reconstructed 3D image. In embodiments wherein a plurality of scout images are used, the more exposure parameter values held constant across the plurality of scout images, including emitter current, emitter voltage, field of view size, and image resolution, make the determinations of physical characteristics more straight forward and therefore would require less calibration and/or compensation, in order to make the determinations of physical characteristics.

At 306 a user input of desired image quality is received. As previously noted, one potential benefit of certain embodiments as disclosed herein is to decrease user dependence upon technical knowledge and experience in order to select proper imaging exposure parameter values. Therefore, in one embodiment, and as depicted in the user interface of FIG. 6, the user inputs a selection of a desired low, medium, or high quality 3D reconstruction, depending upon the purposes for which the 3D reconstruction is being used, and/or the image quality needs. In some embodiments, image quality may represent, fully or partially, an acceptable level of noise in the plurality of projection images or the resulting 3D reconstruction. For example, the user input of desired quality at 306 can comprise a selection of high, medium, or low level of noise, or a specific signal to noise ratio that is acceptable to the user.

At 308 at least one exposure parameter value is determined. The at least one exposure parameter value may be determined at 308 in a variety of ways. In one embodiment, the exposure parameter value may be determined based upon a determined physical characteristic of total attenuation determined at 304 and the field of view size in order to generate either a projection image or a reconstruction 3D image with a predetermined acceptable noise level. In another embodiment, the user input/selection of desired quality is used to define the acceptable noise level. This embodiment provides the user with additional control over the automatically determined at least one exposure parameter value. In an exemplary embodiment, the at least one exposure parameter value is emitter current. In an exemplary optional embodiment, at 310 a user input of desired resolution is received. The noise level in the reconstructed image can also be affected by the use of noise reduction software filtration. The noise reduction software filtration "softens" or blurs the reconstructed image thus reducing resolution by averaging across pixel values. By reducing magnitude of differences between pixels, and therefore the overall noise in the images, noise reduction software filtration enables achievement of a same level of noise with reduced emitter current and patient dose, albeit typically with reduced resolution. Therefore, if, by inputting a desired resolution at 310, the user indicates that a reduced resolution is acceptable, then the emitter current and overall patient dose may be reduced further than would have been determined from the physical characteristics and desired image quality alone.

In exemplary embodiments, the user input of desired resolution may be a user selection of a high resolution, normal resolution, or low resolution. Since the resolution in the context of these embodiments can be affected by noise-reduction software filtration, in an additional embodiment, the user input of desired resolution may be an indication of whether or not to use noise reduction software filtering, as shown exemplarily in the user input controls of FIG. 6. In still further embodiments, a user input of a low, medium, or high level of software filtering may also be received.

After the user input of desired resolution is received at 310, suitable noise filtering is determined. Exemplarily, as disclosed above, low, medium, and high degrees of noise reduction software filtering may be available, and one or more of these options may be selected by the user. In an additional embodiment, the measured total attenuation as determined at 304 may be used to automatically determine the suitable noise filtering. In most cases, the reconstruction image will be blurred more by stronger projection image noise reduction software filtering than by a lower level of noise reduction software filtering. The stronger noise filtering will also have the most impact in reducing noise level. Therefore, in most cases, the lower total attenuation (e.g. from a child's head) will result in selection of a lower noise reduction software filtering, whereas an image with more total attenuation (e.g. an image of an adult head) can be processed with a higher level of noise reduction software filtering to achieve similar image exposure values.

Figure 12:
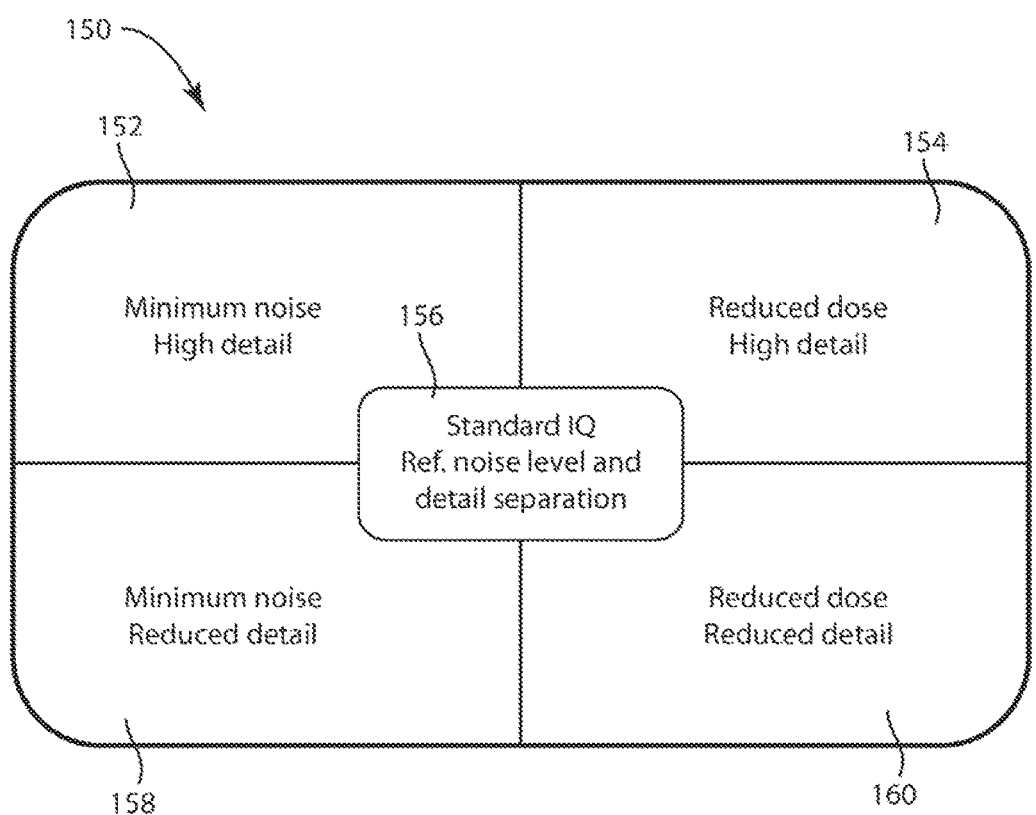
FIG. 12 is an exemplary embodiment of a graphical user interface (GUI) as may be used as an input device in connection with systems and methods.

FIG. 12 depicts a merely exemplary embodiment of a portion of a graphical user interface 150 configured to receive a user input selection of an image quality. In an exemplary embodiment, the GUI 150 is an additional embodiment to the desired image quality GUI 120 described above with respect to FIG. 6. In the GUI 150, an exemplary five options are presented to the user in "effective" terms rather than "technical" terms of actual imaging parameter values. These options include "Minimum Noise, High Detail" 152, "Reduced Dose, High Detail" 154, "Standard Image Quality" 156, "Minimum Noise, Reduced Detail" 158, and "Reduced Dose, Reduced Detail" 160. In an embodiment, the five options presented above represent a descending order of dose and an increasing order of image filtration, as explained above. Options 152 and 154 offer lower noise filtration, resulting in the "High Detail" indication, while options 158 and 160 offer increased noise filtration indicated by "Reduced Detail." Comparatively, options 152 and 158 use higher emitter currents ("Minimum Noise") than options 154 and 160, respectively ("Reduced Dose"). The "Standard Image Quality" option 156, represents a balance between dose and detail.

Referring back to FIG. 10, an embodiment wherein noise reduction software filtering is used, as noted above, in the system can employ reduced emitter current, thus resulting in a lower patient dose. Therefore, the use and strength of noise reduction software filtering can further be used in embodiments at 308 to determine the at least one exposure parameter value. In some embodiments, the exposure parameter value may be presented at 312, exemplarily on a graphical display, and further exemplarily in GUI 77, as the actual numerical values that are determined at 308 and thereafter used by the imaging apparatus. In an alternative embodiment, the exposure parameter value may be indicated to the user on relative terms. In a non-limiting example, if the exposure parameter is emitter current, the user may be presented with information indicating whether a low, medium, or high emitter current has been determined for use in the acquisition of the projection images.

In some embodiments, next at 314, the determined at least one exposure parameter value and a determined noise reduction software filtering, if any, are presented to the user for confirmation. In some embodiments, it may be desirable to present to the user the determined exposure parameter value and/or use of noise reduction software filtering. Not only does this give the user the opportunity to confirm the use of these functions to achieve dose control, but can also serve to educate the user such that over time the user becomes more experienced with the noise reduction software filtering selections and exposure parameter values that achieve the user inputs of desired image quality and/or desired resolution for a patient of the present physical characteristics.

At 316 the imaging apparatus is operated to acquire a plurality of projection images using the determined at least one exposure parameter. In an exemplary embodiment, the at least one exposure parameter is an emitter current and the imaging apparatus operates the emitter with the determined value for the emitter current in order to obtain the plurality of projection images.

In embodiments wherein noise reduction software filtering has been determined for use, then at 318 the determined noise filter is used to filter the projection images. As noted above, filtering of the projection images averages or smooths pixel values across an acquired image, typically reducing resolution but improving noise level. Finally, at 320 a 3D image is reconstructed from the plurality of projection images. As detailed above, with respect to FIG. 9, a variety of 3D image reconstruction techniques are available and may be used in exemplary embodiments of the method 300.

In an additional exemplary embodiment, after the at least one scout image is acquired at 302, as described above, a rough estimation may be made about the gray values of the target volume. The gray values may be estimated by back-projection the scout images before the actual acquisition of the projection images. In a still further additional embodiment, the scout images may first be down-sampled (and/or averaged) before the scout images are back-projected. In a still further additional embodiment, the scout images and/or the back-projected images may be processed (e.g. down-sampled and/or averaged). Next, secondary estimations such as minimum, maximum, difference, mean, or median estimations of gray values can be calculated from the back-projected scout images. The secondary estimations of gray values are used at 308 to determine at least one imaging parameter (e.g. emitter current (mA), number of images, or KVS) and/or image processing parameters (e.g. pre-processing filter, MAR) that are used for the actual acquisition of the projection images. In an embodiment, these estimations of gray values from 322 can be used as the determined physical characteristics, or as an independent value used in the determination of at least one imaging parameter at 308.

FIG. 11 is a flow chart of an exemplary embodiment of a method 400 of automatic dose control in an X-ray imaging apparatus.

It will be noted that portions of the method 400 are similar to those as described above and particularly with respect to the methods 200 and 300. In general, the method 400 discloses an exemplary embodiment of a method wherein the scout images are acquired in the course of an imaging procedure to capture a plurality of projection images. In this context, the scout images can be projection images acquired during an imaging procedure which may be used in a 3-D reconstruction. In some non-limiting embodiments, the method of automatic dose control can be performed during an imaging procedure in some non-limiting embodiments, the method of automatic dose control may be performed at other times in an imaging procedure apart from, or in addition to any automatic dose control performed at the start of an imaging procedure. In the method 400, a user input of desired image quality is received at 402. This user input of desired image quality may exemplarily be received through the GUI as described about with respect to FIG. 6, and as described in further detail with respect to FIG. 10. Also, at 404 some embodiments of the method 400 may further receive a user input of desired resolution as described above with respect to FIG. 10. After the user input of desired image quality and/or desired resolution have been received, a 3D imaging procedure is initiated at 406. The 3D imaging procedure includes the acquisition of a plurality of projection images. As will be described with respect to method 400 herein, in an exemplary embodiment, the plurality of projection images are acquired in two portions. At 408 the imaging apparatus acquires at least one scout image as a first portion of the plurality of projection images. The at least one scout image is acquired at an angle relative to the object to be imaged (e.g. patient's head) that is suitable for representing the physical characteristics of the object to be imaged. In embodiments, two or more scout images are acquired and in a further embodiment, at least two of the acquired scout images are generally orthogonal to one another.

The at least one scout image acquired as the first portion of the plurality of projection images is analyzed at 410 to determine at least one physical characteristic of the object to be imaged. As described above, the at least one physical characteristic may be a size, density and/or attenuation of the object to be imaged. The determination of the at least one physical characteristic at 410 is facilitated by the at least one scout image being acquired at 408 at known exposure parameter values and may be further facilitated by calibration of the known exposure parameter values, for example, by comparing the actual scout image(s) to expected image results from an object with known physical characteristics. These calibrations and relationships may be experimentally determined or modeled and stored at the computer processor, or memory communicatively connected to the computer processor.

Once the at least one physical characteristic is determined at 410, at least one exposure parameter value can be determined at 412. The determination of the at least one exposure parameter value from the at least one physical characteristic has been explained above. In embodiments, the at least one exposure parameter value may be determined solely from the at least one physical characteristic, or in combination with additional information, which in embodiments may include the user input of desired image quality received at 402. In still further embodiments, if a user input of desired resolution was received at 404, then at 414 a level of noise filtering that will achieve the user input of desired resolution is determined. As detailed above, if noise filtering is used, this may further enable the reduction of patient dose and therefore at 412 may result in the determination of an exposure parameter value that is less than if no noise filtering were used.

After the at least one exposure parameter value is determined at 412, the control circuit operates the imaging apparatus to adjust at least one exposure parameter to the values determined at 412. After adjusting the at least one exposure parameter value at 416, the imaging apparatus operates at 418 to acquire a second portion of the plurality of projection images. The second portion of the plurality of projection images completes the acquisition of the plurality of projection images to be used in the 3D reconstruction. In an embodiment, although the first portion of the plurality of projection images may, optionally, be a relatively small number, the second portion of the plurality of projection images acquired with the adjusted at least one exposure parameter value, may, in exemplary embodiments, be 100 or more projection images.

In embodiments wherein noise filtering has been selected (e.g., by the user), the plurality of projection images are filtered at 420 in order to improve the noise level in the projection images and improve the noise level in the resulting 3D reconstruction. Finally, whether the plurality of projection images is filtered or not, a 3D image is created at 422 from the plurality of projection images exemplarily by known reconstruction techniques.

As will be understood by those having ordinary skill in the art, the present disclosure thus provides examples of X-ray imaging systems that comprise an imaging apparatus having emitter emitting X-rays through an object and a receiver receiving the X-rays, and a control circuit controlling the emitter and processing the X-rays received by the receiver to generate X-ray images of the object. Specific examples of the imaging apparatus and control circuit are described with reference to the attached drawing Figures. These examples are not limiting, and the concepts of the present disclosure are applicable to other types of imaging apparatus having different configurations of control circuitry. In examples discussed herein, the control circuit determines at least one exposure parameter value. In some embodiments, this is achieved through user selection of desired quality and physical characteristics based on analysis of at least one scout image. In an additional exemplary embodiment, this may be performed during an imaging procedure.

The inventors have observed that the selection of X-ray exposure parameter values can sometimes require considerable operator experience to achieve the desired image quality while avoiding excessive X-ray exposure to the patient. Operators who perform a particular type of X-ray imaging infrequently may not have this operator experience. Unnecessarily high emitter current selection increases patient dose, while excessively low emitter current selection can result in insufficient image quality (e.g., excessive image noise). Furthermore, if the image quality is insufficient, the operator may need to conduct an additional imaging session, resulting in additional patient dose. Certain embodiments of systems and methods as disclosed herein can perform automatic dose control (ADC) that automatically calculates at least one optimal exposure parameter value based upon at least one physical characteristic determined from at least one scout image. In embodiments, the system and methods may further determine an optimal level of noise filtering in conjunction with the at least one exposure value, which may result in further reductions in patient dose.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of steps, it is to be understood and appreciated that the methodologies are not limited by the order of steps, as some steps may, in accordance therewith, occur in a different order and/or concurrently with other steps from that shown and described herein. For example, those skilled in the art will understand and appreciate that a methodology can also be represented as a series of interrelated states or events, such as in a state diagram. Moreover, in some implementations, not all of the illustrated acts or steps are required.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they have equivalent elements.

What is claimed is:

1. A method of dose control in three-dimensional X-ray imaging, the method comprising:
   acquiring at least one image of an object with an X-ray emitter and an X-ray receiver;
   determining with at least one computer processor image data from the at least one image, wherein the image data is a level of noise in the at least one image;
   determining with the at least one computer processor at least one imaging parameter value based upon the level of noise and a dose parameter;
   acquiring with the X-ray emitter and X-ray receiver a plurality of projection images of the object using the at least one imaging parameter value; and
   reconstructing with the at least one computer processor a three-dimensional X-ray image from the plurality of projection images.

2. The method of claim 1, wherein the at least one imaging parameter value comprises an emitter current.

3. The method of claim 1, wherein the at least one image comprises a plurality of images acquired at least one of a predetermined imaging parameter, a predetermined field of view (FOV) size, and a predetermined resolution.

4. The method of claim 1, further comprising receiving a user input of an image quality of the three-dimensional X-ray image as the dose parameter, wherein at least one imaging parameter value is further determined by the at least one computer processor based upon the user input of the image quality of the three-dimensional X-ray image.

5. The method of claim 4, further comprising:
   receiving a user input of image resolution;
   selecting with the at least one computer processor a noise filter based upon the received user input of image resolution; and
   filtering the plurality of projection images with the noise filter before reconstructing the three-dimensional X-ray image from the acquired plurality of projection images.

6. The method of claim 5, wherein at least one exposure parameter value is further determined by the at least one computer processor based upon the noise filter selected by the computer processor.

7. The method of claim 1, further comprising:
   determining, with the at least one computer processor, an attenuation value of an object in the at least one image; and
   determining, with the at least one computer processor, at least one imaging parameter value based upon the attenuation of the object in the at least one image.

8. The method of claim 1, wherein the at least one image is acquired at an initial emitter current, the method further comprising:
   initiating a three-dimensional imaging procedure to capture a plurality of procedure images wherein the at least one image comprises a first portion of the plurality of procedure images and the plurality of projection images are a second portion of the plurality of procedure images; and
   adjusting the at least one imaging parameter value to an emitter current value determined by the at least one computer processor;
   wherein the plurality of projection images are acquired at the emitter current value determined by the at least one computer processor and the at least one computer processor reconstructs the three-dimensional X-ray image from the plurality of procedure images.

9. The method of claim 1, further wherein determining image data from the at least one image comprises estimating at least one gray value of a target volume from the at least one image, wherein the at least one imaging parameter is further determined based upon the at least one gray value.

10. The method of claim 1, wherein the at least one imaging parameter value is an emitter current and further comprising:
   selecting a noise filter based upon a predetermined image resolution; and
   filtering the plurality of projection images with the noise filter before reconstructing the three-dimensional X-ray image from the acquired plurality of projection images.

11. The method of claim 1, wherein the dose parameter is a level of noise for the three-dimensional X-ray image.

12. A method of exposure control in three-dimensional X-ray imaging, the method comprising:
   acquiring at least one image with an X-ray emitter and an X-ray receiver, the X-ray emitter operating at an initial imaging parameter value;
   determining a level of noise in the at least one image with at least one computer processor;
   determining with the at least one computer processor a new emitter current value based at least upon the level of noise and an image quality of a three-dimensional X-ray image, wherein the level of noise is a level of noise attributable to the X-ray receiver;
   acquiring with the X-ray emitter and X-ray receiver a plurality of projection images of an object using the X-ray emitter operating at the new emitter current value; and
   reconstructing with the at least one computer processor the three-dimensional X-ray image from the acquired plurality of projection images.

13. The method of claim 12, further comprising:
   receiving a user input of image resolution;
   selecting with the at least one computer processor a noise filter based upon the received user input of image resolution; and
   filtering the plurality of projection images with the noise filter before reconstructing the three-dimensional X-ray image from the acquired plurality of projection images;

wherein the new emitter current value is further determined by the at least one computer processor based at least upon the noise filter selected by the at least one computer processor.

14. The method of claim 12, wherein the at least one image is acquired at a predetermined field of view (FOV) size and a predetermined resolution.

15. An X-ray imaging system, the system comprising:
an X-ray emitter configured to produce X-rays and direct the X-rays toward an object;
an X-ray receiver configured to receive X-rays from the X-ray emitter, wherein the X-ray emitter and X-ray receiver are configured to acquire at least one image of the object; and
at least one computer processor communicatively connected to the X-ray emitter and the X-ray receiver, the at least one computer processor configured to determine a level of noise from the at least one image, and to determine an emitter current value based at least on the level of noise and a level of noise for a three-dimensional X-ray image;
wherein the X-ray emitter and X-ray receiver are further configured to acquire a plurality of projection images of the object using the determined emitter current value, and wherein the at least one computer processor is further configured to reconstruct the three-dimensional X-ray image from the acquired plurality of projection images.

16. The X-ray imaging system of claim 15 wherein the three-dimensional X-ray image is reconstructed by the at least one computer processor from the at least one image of the object and the acquired plurality of projection images.

17. The X-ray imaging system of claim 15, further comprising an input device communicatively connected to the at least one computer processor and configured to receive a user input of the image quality of the three-dimensional X-ray image, wherein the at least one computer processor is further configured to determine the emitter current value based at least on the user input of image quality.

18. The X-ray imaging system of claim 17, wherein the input device is further configured to receive a user input of image resolution and the at least one computer processor is further configured to select a noise filter based upon the received user input of image resolution and to filter the plurality of projection images with the noise filter before reconstructing the three-dimensional X-ray image from the acquired plurality of projection images.

19. The X-ray imaging system of claim 15, wherein the at least one computer processor is further configured to determine an attenuation of the object and to determine the emitter current from the level of noise and the attenuation of the object, and wherein the at least one image is acquired at a predetermined field of view (FOV) size and a predetermined resolution.

* * * * *